(12) United States Patent
Dellinger et al.

(10) Patent No.: US 7,854,610 B2
(45) Date of Patent: Dec. 21, 2010

(54) ORTHODONTIC TOOTH RETENTION SYSTEM

(76) Inventors: Eugene L. Dellinger, 1326 Old Lantern Trail, Fort Wayne, IN (US) 46845; Aron E. Dellinger, 15711 Viberg Rd., Leo, IN (US) 46765

(*) Notice: Subject to any disclaimer, the term of this patent is extended or adjusted under 35 U.S.C. 154(b) by 10 days.

(21) Appl. No.: 11/969,423

(22) Filed: Jan. 4, 2008

(65) Prior Publication Data
US 2008/0176180 A1    Jul. 24, 2008

Related U.S. Application Data

(63) Continuation-in-part of application No. 11/689,674, filed on Mar. 22, 2007, now abandoned, which is a continuation-in-part of application No. 11/122,946, filed on May 5, 2005, now abandoned.

(51) Int. Cl.
*A61C 3/00* (2006.01)
(52) U.S. Cl. .................. 433/18; 433/3; 433/24
(58) Field of Classification Search .......... 433/3, 433/24, 163, 18
See application file for complete search history.

(56) References Cited

U.S. PATENT DOCUMENTS

| | | | |
|---|---|---|---|
| 351,065 A | 10/1886 | Miller | |
| 532,722 A | 1/1895 | Dennis | |
| 3,353,271 A | 11/1967 | Blechman | |
| 3,890,714 A | 6/1975 | Gores | |
| 3,984,915 A | 10/1976 | Noble et al. | |
| 4,014,096 A | 3/1977 | Dellinger | |
| 4,015,333 A | 4/1977 | Dellinger et al. | |
| 4,017,973 A | 4/1977 | Nelson | |
| 4,183,141 A | 1/1980 | Dellinger et al. | |

(Continued)

FOREIGN PATENT DOCUMENTS

EP    1658822 A2    5/2006

(Continued)

OTHER PUBLICATIONS

The International Search Report mailed Jun. 13, 2008, in related International Application No. PCT/US2008/051914.

(Continued)

*Primary Examiner*—Ralph A Lewis
*Assistant Examiner*—Eric Rosen
(74) *Attorney, Agent, or Firm*—Baker & Daniels LLP

(57) ABSTRACT

A method and apparatus for delivering an orthodontic retainer system wherein pairs of magnets are applied to adjacent teeth in a patient's mouth. The retainer system may include a pair of dental modules, in the form of mutually attracted members, that are temporary retained on a delivery member and positioned on a patient's teeth. In one exemplary embodiment, the dental modules have rounded and/or chamfered edges and a sloped lingual surface. In one exemplary embodiment, the delivery member is substantially L-shaped. Advantageously, the substantially L-shape of the delivery member allows an orthodontist to enter only a small portion of the patient's oral cavity to position the dental modules on a patient's teeth. Further, the substantially L-shape of the delivery member eases the orthodontist's delivery of the dental modules into a patient's mouth by substantially eliminating the need for the orthodontist to manipulate or otherwise move the patient's lips, tongue, and/or cheeks.

21 Claims, 12 Drawing Sheets

U.S. PATENT DOCUMENTS

| | | | |
|---|---|---|---|
| 4,243,386 A | 1/1981 | Kawaguchi | |
| 4,284,405 A | 8/1981 | Dellinger | |
| 4,311,463 A | 1/1982 | Glattly | |
| 4,360,341 A | 11/1982 | Dellinger | |
| 4,384,854 A | 5/1983 | Garfinkel | |
| 4,396,373 A | 8/1983 | Dellinger | |
| 4,424,030 A | 1/1984 | Smiley et al. | |
| 4,457,707 A | 7/1984 | Smiley | |
| 4,508,505 A | 4/1985 | Smiley et al. | |
| 4,511,330 A | 4/1985 | Smiley et al. | |
| 4,526,540 A | 7/1985 | Dellinger | |
| 4,551,096 A | 11/1985 | Dellinger | |
| 4,565,526 A | 1/1986 | Kawata et al. | |
| 4,609,350 A | 9/1986 | Krause | |
| 4,657,508 A | 4/1987 | Dellinger | |
| 4,671,767 A | 6/1987 | Blachman et al. | |
| 4,749,352 A | 6/1988 | Nicholson | |
| 4,813,869 A | 3/1989 | Gatewood | |
| 4,869,667 A | 9/1989 | Vardimon | |
| 4,871,310 A | 10/1989 | Vardimon | |
| 4,968,248 A | 11/1990 | McColgan et al. | |
| 5,002,077 A | 3/1991 | Wiley | |
| 5,205,736 A | 4/1993 | Blechman | |
| 5,305,768 A * | 4/1994 | Gross et al. | 132/321 |
| 5,334,015 A | 8/1994 | Blechman | |
| 5,362,769 A | 11/1994 | Waller et al. | |
| 5,678,998 A | 10/1997 | Honkura et al. | |
| 5,752,832 A | 5/1998 | Vardimon et al. | |
| 5,782,743 A * | 7/1998 | Russell | 600/9 |
| 5,788,493 A * | 8/1998 | Tanaka et al. | 433/189 |
| 5,954,506 A | 9/1999 | Tanaka | |
| 6,299,450 B1 | 10/2001 | Honkura et al. | |
| 6,382,965 B1 | 5/2002 | Ruiz-Vela et al. | |
| 6,390,812 B1 | 5/2002 | Chishti et al. | |
| 6,413,086 B1 * | 7/2002 | Womack | 433/72 |
| 6,485,298 B2 | 11/2002 | Chishti et al. | |
| 6,705,863 B2 | 3/2004 | Phan et al. | |
| 6,984,128 B2 | 1/2006 | Breining et al. | |
| 7,300,279 B2 | 11/2007 | Amundsen | |
| 2002/0137010 A1 | 9/2002 | Honkura et al. | |
| 2003/0124478 A1 | 7/2003 | Amundsen | |
| 2004/0054028 A1 | 3/2004 | Hattori | |
| 2004/0229191 A1 * | 11/2004 | Dietrich | 433/159 |
| 2005/0100868 A1 | 5/2005 | Karim et al. | |
| 2005/0133058 A1 * | 6/2005 | Ding | 132/323 |
| 2005/0186526 A1 | 8/2005 | Stewart et al. | |
| 2006/0240373 A1 | 10/2006 | Amundsen | |
| 2006/0252001 A1 | 11/2006 | Dellinger | |
| 2007/0020583 A1 | 1/2007 | Kojima | |
| 2007/0065768 A1 | 3/2007 | Nadav | |
| 2007/0190476 A1 | 8/2007 | Dellinger | |
| 2008/0108007 A1 | 5/2008 | Kong et al. | |
| 2008/0199824 A1 * | 8/2008 | Hargadon | 433/6 |

FOREIGN PATENT DOCUMENTS

| | | |
|---|---|---|
| EP | 1278477 B1 | 8/2006 |
| EP | 1723925 B1 | 9/2007 |
| WO | WO2008/115616 A1 | 9/2008 |

OTHER PUBLICATIONS

Sandler, P.J. et al., Magnets and Orthodontics, British Journal of Orthodontics, vol. 16 (1989), pp. 243-249. (Sandler).

Noar, J.H. et al., Rare Earth Magnets in Orthodontics: An Overview, British Journal of Orthodontics, vol. 26 (1999), pp. 29-37. (Noar).

Springate. S.D. et al., Micro-magnetic Retainers: An Attractive Solution to Fixed Retention, British Journal of Orthodontics, vol. 18 (1991), pp. 139-141. (Springate).

Donohue, V.E. et al., In Vitro Cytotoxicity Testing of Neodymium-Iron-Boron Magnets, Journal of Applied Biomaterials, vol. 6 (1995), pp. 69-74. (Donahue).

Darendeliler, A., Clinical application of magnets in orthodontics and biological implications: a review, European Journal of Orthodontics, vol. 19 (1997), pp. 431-442 (Darendililer).

Blechman, A.M., Pain-free and mobility-free orthodontics?, American Journal of Orthodontics and Dentofacial Orthopedics (1998), pp. 379-383. (Blechman).

* cited by examiner

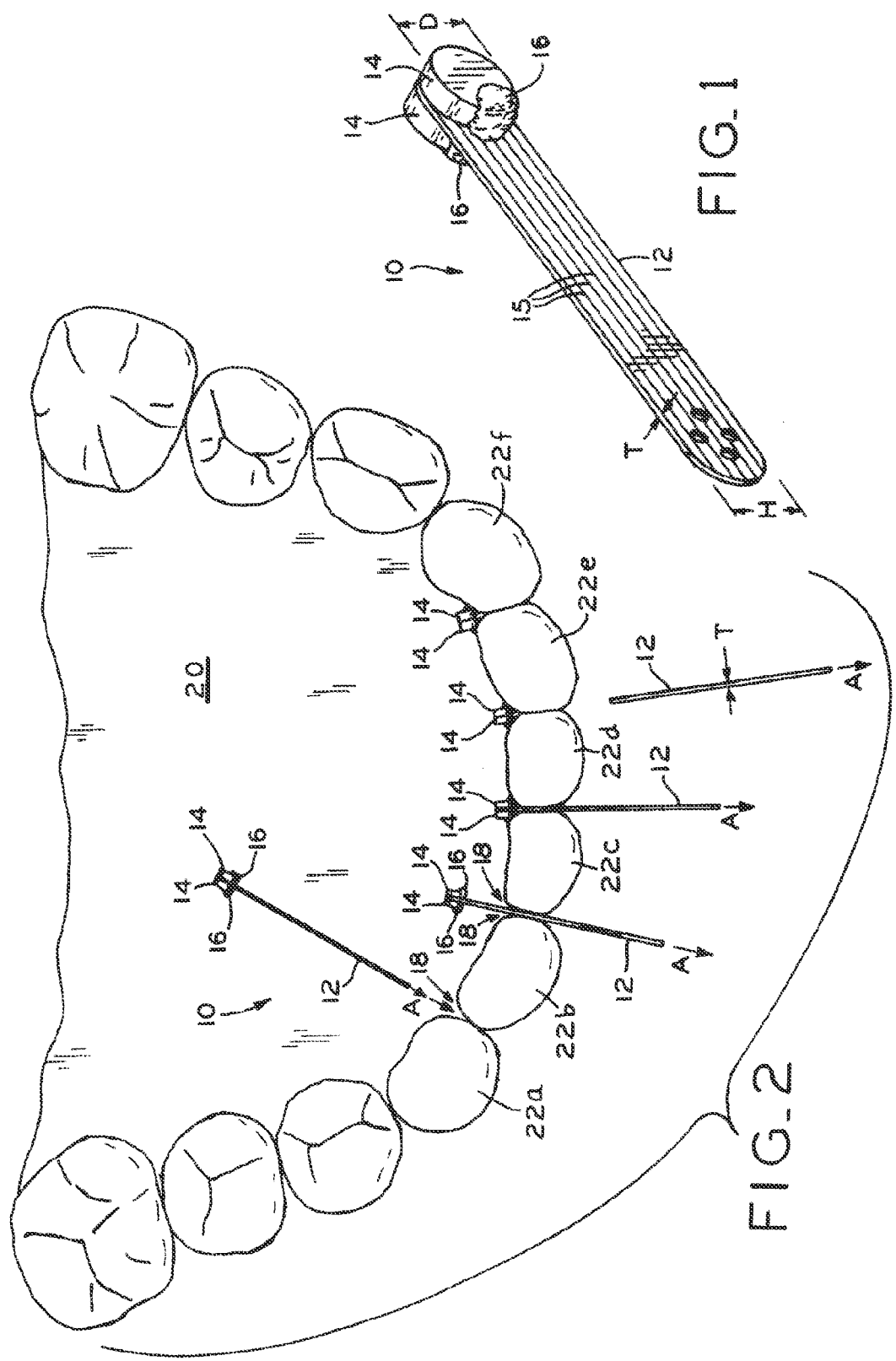

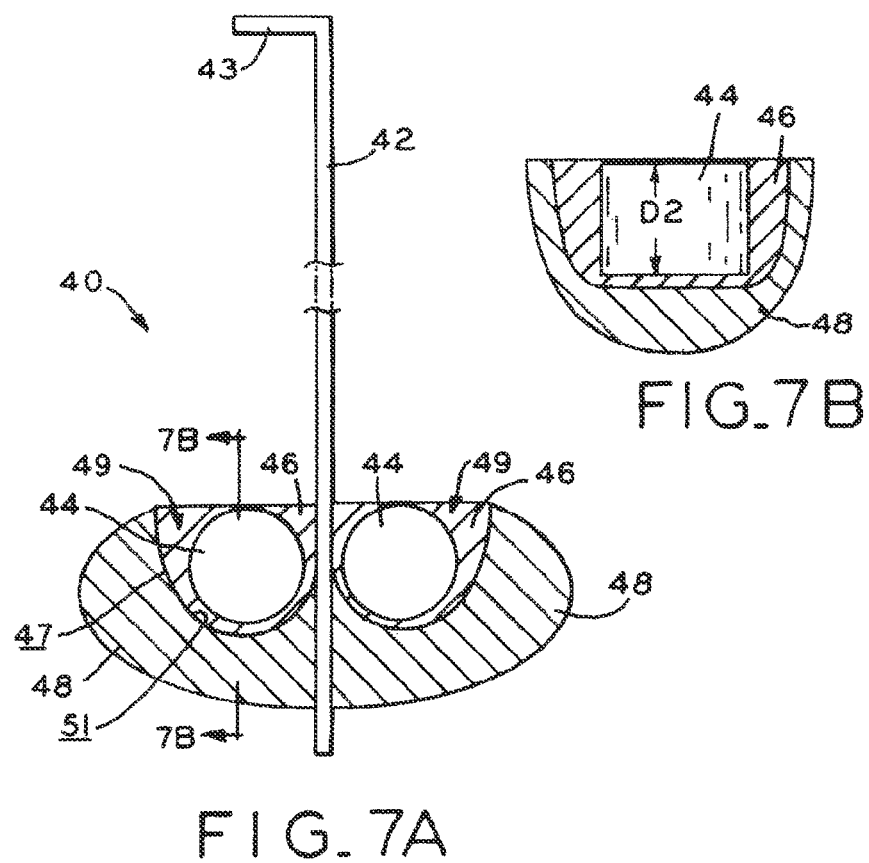
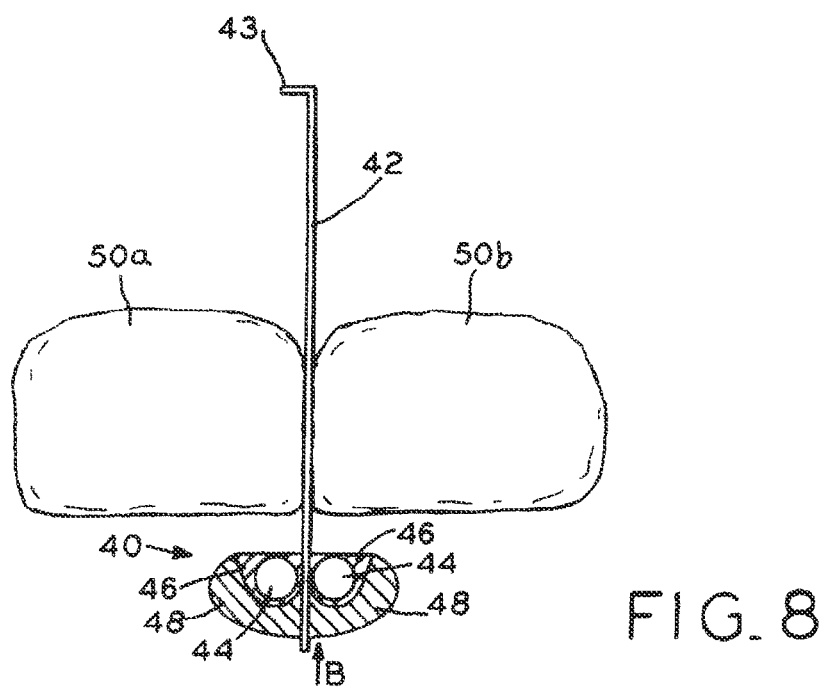

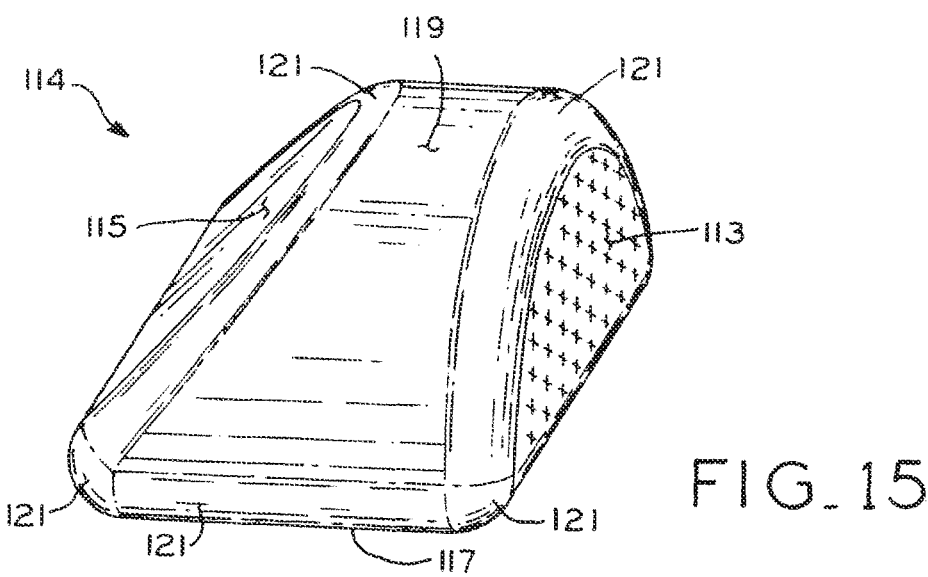
FIG_15
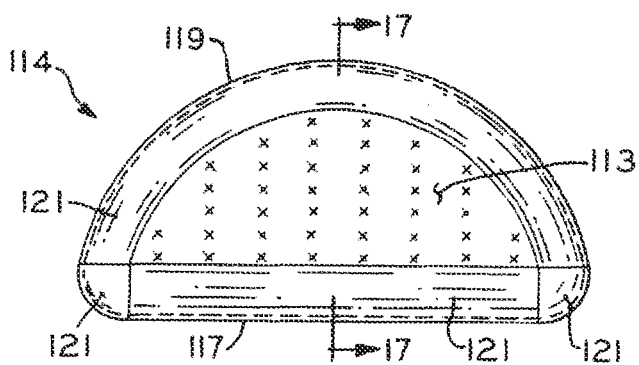
FIG_16
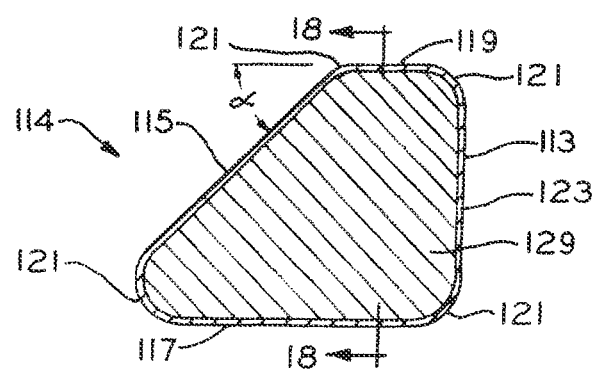
FIG_17
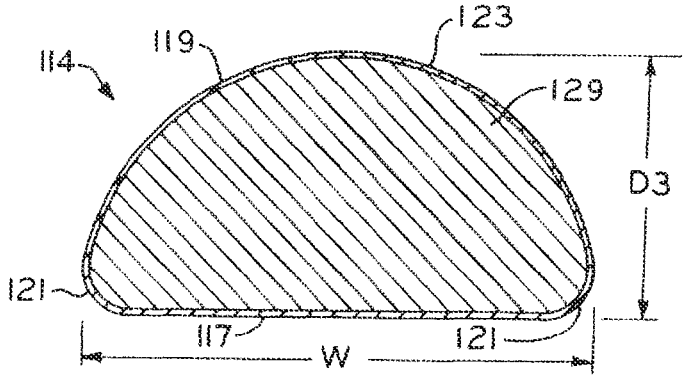
FIG_18

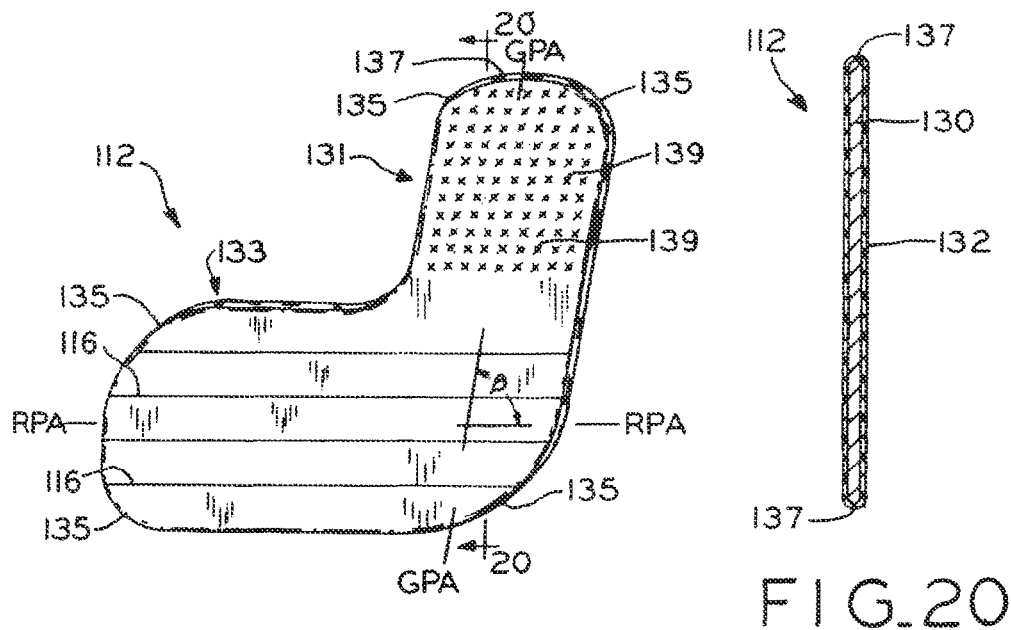
FIG.19
FIG.20
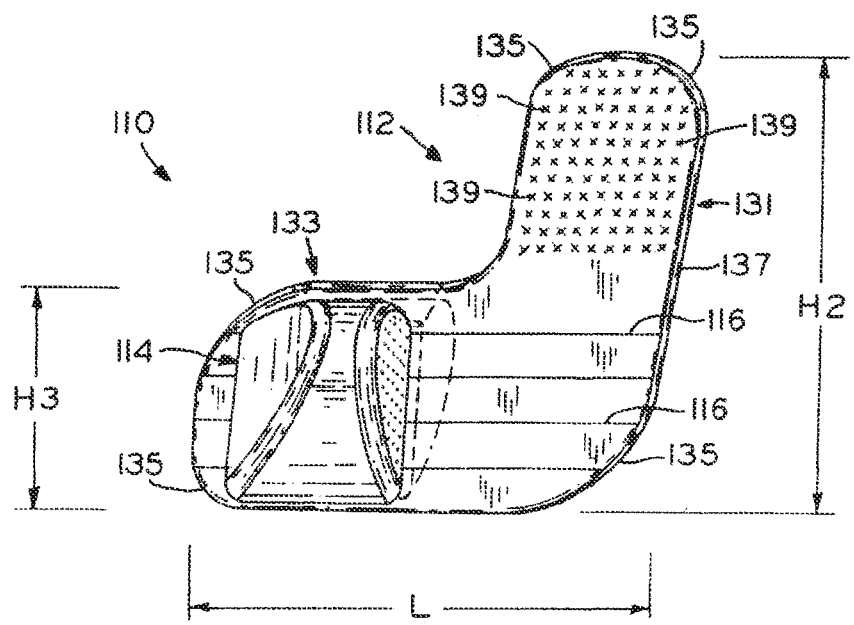
FIG.21

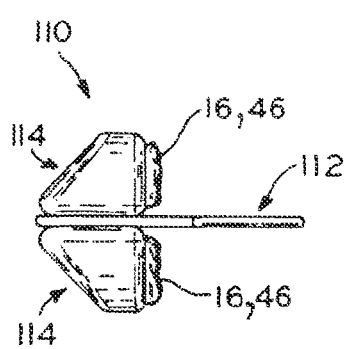
FIG. 24
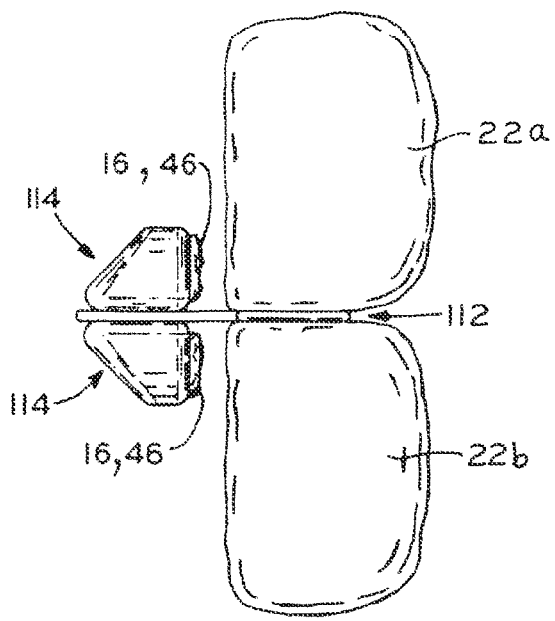
FIG. 25
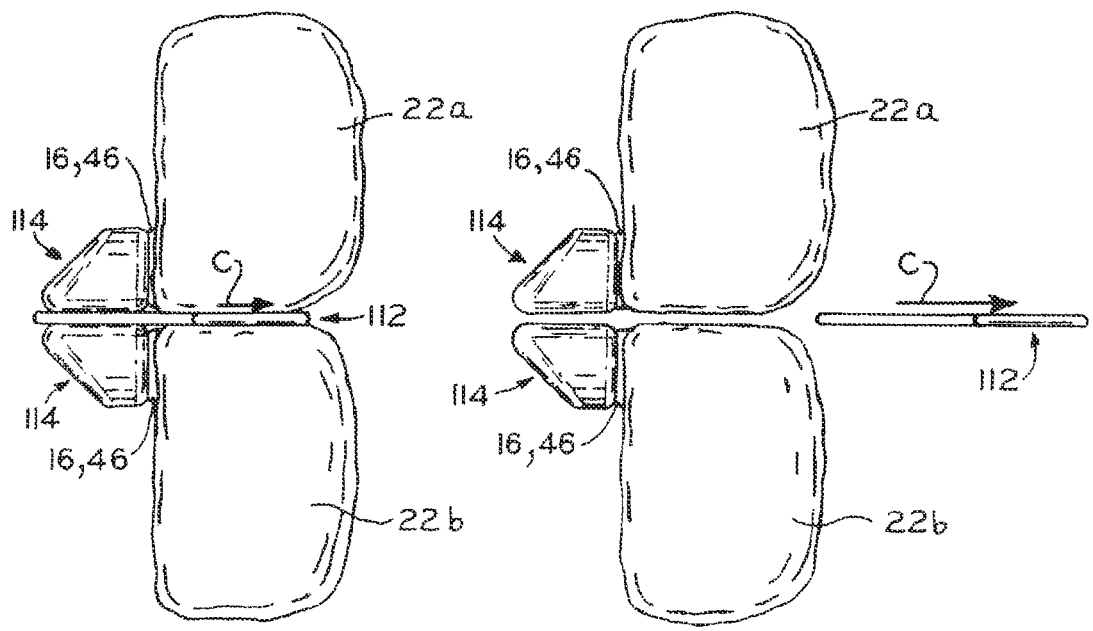
FIG. 26
FIG. 27

ORTHODONTIC TOOTH RETENTION SYSTEM

CROSS REFERENCE TO RELATED APPLICATIONS

This application is a continuation-in-part of co-pending U.S. patent application Ser. No. 11/689,674, filed Mar. 22, 2007, entitled ORTHODONTIC TOOTH RETENTION SYSTEM, which is a continuation-in-part of U.S. patent application Ser. No. 11/122,946, filed May 5, 2005, entitled METHOD AND APPARATUS FOR POSITIONING AN ORTHODONTIC APPLIANCE, now abandoned, the entire disclosures of which are hereby expressly incorporated herein by reference.

BACKGROUND

1. Field of the Disclosure

The present disclosure relates to orthodontics, and, more particularly, to an orthodontic tooth retention system for delivering pairs of magnets for application to adjacent teeth to retain the teeth in a desired position.

2. Description of the Prior Art

Many types of orthodontic appliances incorporating a variety of arrangements of mutually attracted elements, such as magnets, have been proposed. Some prior arrangements use magnets as a retaining device to retain teeth in a corrected position as a secondary function to primary tooth movement. Magnetic elements have also been used in combination with dentures for retaining the dentures in the mouth. When magnets are used as retaining devices, the magnets are placed onto teeth and the attractive force between the magnets provides a retaining force, thereby preventing the adjacent teeth from moving apart.

Other arrangements use magnets as corrective devices to move teeth into a corrected position. The conventional way for moving teeth in the mouth usually involves orthodontic appliances, such as braces and wires that exert a constant force on the tooth that needs to be moved. An elastic member creating the constant force must periodically be adjusted by a dentist or orthodontist. Many times dental appliances, including a retainer wire, are required across the front of the teeth to prevent excessive movement of the teeth.

SUMMARY

The present disclosure provides a method and apparatus for delivering an orthodontic retainer system wherein pairs of magnets are applied to adjacent teeth in a patient's mouth. The retainer system may include a pair of dental modules, in the form of mutually attracted members, that are temporary retained on a delivery member and positioned on a patient's teeth. In one exemplary embodiment, the dental modules have rounded and/or chamfered edges and a sloped lingual surface. In one exemplary embodiment, the delivery member is substantially L-shaped. Advantageously, the substantially L-shape of the delivery member allows an orthodontist to enter only a small portion of the patient's oral cavity to position the dental modules on a patient's teeth. Further, the substantially L-shape of the delivery member eases the orthodontist's delivery of the dental modules into a patient's mouth by substantially eliminating the need for the orthodontist to manipulate or otherwise move the patient's lips, tongue, and/or cheeks.

In one exemplary embodiment, the retainer system includes a magnet carrier portion having a recess which contains an adhesive material. The magnets may be embedded in the adhesive material. Once positioned on adjacent teeth, the adhesive material is cured and the carrier is removed to reveal an envelope or shaped profile of the adhesive material. The shaped profile of the adhesive material obviates the need to post-form adhesive material around the magnets after attaching the magnets to the adjacent teeth. Furthermore, the shaped profile may include a smooth surface. The adhesive material may also be aesthetically colored to match the coloring of the adjacent teeth. The carrier may be formed of a water soluble material or may be a flexible material.

In one embodiment, a method and apparatus for delivering an orthodontic appliance is provided wherein pairs of mutually attracted members, e.g., magnets, are applied to adjacent teeth, thereby retaining the teeth in a desired position, for example, after the teeth have been moved to new positions by conventional orthodontic techniques. The magnets may be very small magnets which may be gold plated. Generally, the magnets are biocompatible.

In an exemplary embodiment, the method of applying the magnets to the teeth includes placing two magnets on opposite sides of a thin, non-magnetic strip of material, such as Mylar® material, available from DuPont Teijin Films, of Hopewell, Va. Because the magnets are attracted to each other, they will stay in place on opposite sides of the strip. An adhesive is applied to each magnet, and/or to the teeth to which the magnets will be secured. In one exemplary embodiment, primer material is applied to the adjacent teeth in the locations where the magnets are to be placed and the adhesive is applied to the magnets. The strip is then placed in the space between two adjacent teeth. The thin, non-magnetic strip is then drawn forward between the adjacent teeth until the adhesive material on the magnets touches the primer material on the adjacent teeth. This allows ideal positioning of the magnets as determined by their individual magnetic fields. An ultraviolet or visible light source can be used to cure the adhesive, and retain each of the magnets in place on one of the two adjacent teeth. The strip is then removed by pulling it through the space between the adjacent teeth, thereby leaving behind the magnets secured to the adjacent teeth. The magnets will retain the adjacent teeth in their positions because of the magnetic attraction between the magnets.

In one form thereof, the present invention provides an orthodontic retainer system for use on teeth, including: a delivery member, including: a gripping portion extending along a gripping portion axis; and a retention portion extending along a retention portion axis, the gripping portion joined to the retention portion at an angle such that the delivery member is substantially L-shaped; and a pair of dental modules coupled to the delivery member.

In another form thereof, the present invention provides a dental module for use on teeth as part of an orthodontic retainer system, including: a tooth engaging surface; a bottom surface having opposing ends, wherein a distance between the opposing ends of the bottom surface defines a width of the dental module, the bottom surface forming a first angle with the tooth engaging surface; a lingual surface forming a second angle with at least one of the tooth engaging surface and the bottom surface, wherein the second angle is less then ninety degrees; and at least one chamfered edge defined between at least one of the tooth engaging surface, the bottom surface, and the lingual surface and another of the tooth engaging surface, the bottom surface, and the lingual surface.

In yet another form thereof, the present invention provides a method of applying a dental module to a tooth having a lingual side, including the steps of: providing a substantially L-shaped delivery member; positioning at least one dental module on the delivery member; inserting the delivery member between a pair of adjacent teeth; advancing the delivery member in an anterior direction to remove the delivery member from between the pair of adjacent teeth.

BRIEF DESCRIPTION OF THE DRAWINGS

The above mentioned and other features of this disclosure, and the manner of attaining them, will become more apparent and will be better understood by reference to the following description of embodiments of the disclosure taken in conjunction with the accompanying drawings, wherein:

FIG. 1 is a perspective view of a delivery member of the present disclosure, further illustrating a coupled pair of mutually attracted members;

FIG. 2 is an occlusal view of an individual's teeth, further illustrating the several steps of the method of the present disclosure;

FIG. 7A is a partial sectional occlusal view of an orthodontic retainer system according to another embodiment of the present disclosure;

FIG. 7B is a cross-sectional view of a portion of the system of FIG. 7A, taken along line 7B-7B of FIG. 7A;

FIGS. 8-19 are partial sectional occlusal views of exemplary steps in a method of attaching a pair of magnets to a pair of adjacent teeth, wherein:

FIG. 8 shows the pair of magnets spaced from the pair of adjacent teeth before attachment thereto;

FIG. 9 shows the pair of magnets temporarily attached to the pair of adjacent teeth prior to curing the adhesive material;

FIG. 10 shows a curing instrument for curing the adhesive material;

FIG. 11 shows an instrument for dispensing water onto the system;

FIG. 12 shows the carrier partially dissolved;

FIG. 13 shows the carrier completely dissolved to reveal the adhesive material profile;

FIG. 14 shows the removal of an alternative carrier with a dental instrument;

FIG. 15 is a perspective view of a mutually attractive member according to another exemplary embodiment;

FIG. 16 is a lingual view of the mutually attractive member of FIG. 15;

FIG. 17 is a cross-sectional view of the mutually attractive member of FIG. 16 taken along line 17-17 of FIG. 16;

FIG. 18 is a cross-sectional view of the mutually attractive member of FIG. 17 taken along line 18-18 of FIG. 17;

FIG. 19 is a perspective view of a delivery member according to another exemplary embodiment;

FIG. 20 is a cross-sectional view of the delivery member of FIG. 19 taken along line 20-20 of FIG. 19;

FIG. 21 is a perspective view of the delivery member of FIG. 19, further illustrating a pair of coupled mutually attractive members according to the embodiment of FIG. 15;

FIG. 24 is an occlusal view of the delivery member and mutually attractive members of FIG. 23, further illustrating adhesive positioned on the mutually attractive members;

FIG. 25-27 are partial sectional occlusal views of exemplary steps in a method of attaching the pair of mutually attractive members to a pair of adjacent teeth, wherein:

FIG. 25 shows the pair of mutually attractive members spaced from the pair of adjacent teeth before attachment thereto;

FIG. 26 shows the pair of mutually attractive members attached to the pair of adjacent teeth;

FIG. 27 shows the delivery member separated from the pair of mutually attractive members;

Figure 3:
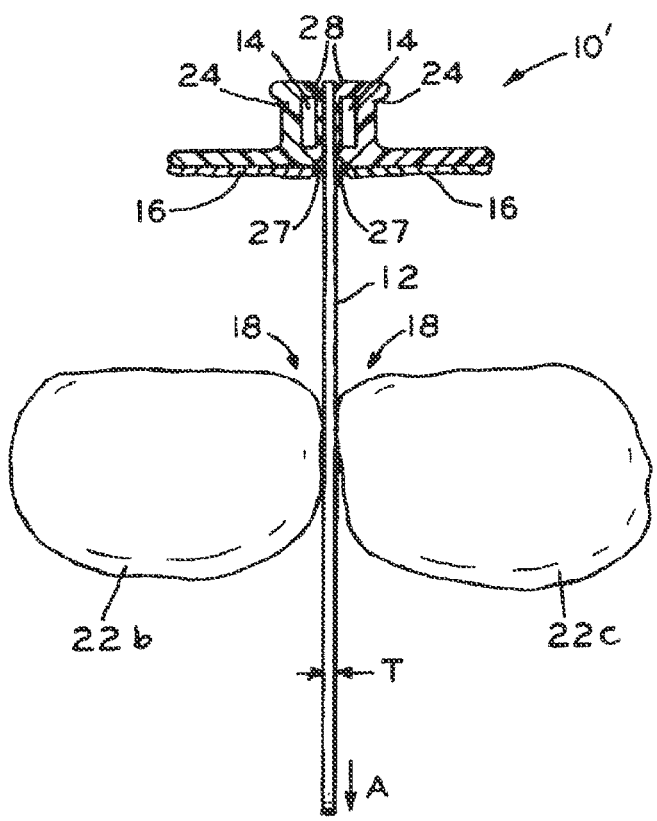
FIG. 3 is an occlusal view of a portion of an individual's teeth, further illustrating an alternative embodiment orthodontic retainer system according to the present disclosure.

Corresponding reference characters indicate corresponding parts throughout the several views. Although the exemplifications set out herein illustrate the disclosure, the embodiments disclosed below are not intended to be exhaustive or to be construed as limiting the scope of the invention to the precise forms disclosed.

DETAILED DESCRIPTION

The present disclosure provides a method and apparatus for delivering an orthodontic retainer system wherein pairs of magnets are applied to adjacent teeth in a patient's mouth. The retainer system may include a pair of dental modules, in the form of mutually attracted members, that are temporary retained on a delivery member and positioned on a patient's teeth. In one exemplary embodiment, the dental modules have rounded and/or chamfered edges and a sloped lingual surface. In one exemplary embodiment, the delivery member is substantially L-shaped. Advantageously, the substantially L-shape of the delivery member allows an orthodontist to enter only a small portion of the patient's oral cavity to position the dental modules on a patient's teeth. Further, the substantially L-shape of the delivery member eases the orthodontist's delivery of the dental modules into a patient's mouth by substantially eliminating the need for the orthodontist to manipulate or otherwise move the patient's lips, tongue, and/or cheeks.

Referring now to FIG. 1, orthodontic retainer system 10 is shown, including strip or delivery member 12 and mutually attracted dental modules 14. Mutually attracted dental modules 14 are releasably coupled by attractive forces to opposite sides of delivery member 12. The phrase "mutually attracted dental modules," for the purposes of this document, generally means two separate bodies which have a mutual attraction for each other and which are suitable for placement in the mouth for a period of time. For example, in one embodiment, each mutually attracted dental module 14 may comprise a magnet or any other suitable device capable of mutual attraction, i.e., electrostatic members. When mutually attracted dental modules 14 are magnets, they are coupled together on delivery member 12 via magnetic forces. Each mutually attracted dental module 14 has a dimension D (FIG. 1), such as a height or a diameter, in the range of 0.010 to 0.040 inches, preferably in the range of 0.038 to 0.039 inches. In one form thereof, mutually attracted dental module 14 is in the shape of a cylinder, as shown in FIG. 1. Mutually attracted dental module 14 may also take different forms, including those having cross-sectional shapes such as various polygonal shapes. Each mutually attracted dental module 14 is made of a biocompatible material to allow its implantation in the mouth for a period of time. For example, each mutually attracted dental module 14 may be gold-plated, or, alternatively, could be comprised entirely of gold. In another embodiment, each mutually attracted dental module 14 comprises neodymium iron. As shown in FIG. 1, a quantity of adhesive 16 can be applied to an anterior face of each mutually attracted dental module 14 to facilitate securement of the same to a tooth.

Referring to FIGS. 1 and 2, delivery member 12 is a thin, non-magnetic strip of material, such as Mylar™ material, having a thickness T which, in one embodiment, may be may be as small as 0.001, 0.002, 0.003, 0.004, or 0.005 inches or as large as approximately 0.012, 0.011, 0.010, 0.009, 0.008, 0.007, or 0.006 inches. Thickness T is such as to allow delivery member 12 to pass between a pair of adjacent teeth 22, for example, teeth 22*a* and 22*b*. The length of delivery member 12 can be any size to facilitate an easy access for an orthodontist for pulling delivery member 12 between a pair of adjacent teeth 22*a* and 22*b*, as will be described hereinbelow. Delivery member 12 may also include scribe marks 15 which may be lettered or numbered accordingly to provide a depth gauge, thereby providing the orthodontist with an indication of the depth of delivery member 12 with respect to adjacent teeth 22. In an alternative embodiment, delivery member 12 may be part of a continuous piece of material which has pairs of mutually attracted dental modules 14 carried thereon at various spaced distances. The orthodontist would then cut the continuous piece of material just beyond the location of mutually attracted dental modules 14 to obtain a single orthodontic retainer system 10. Height H of delivery member 12 may range from 0 to 10 millimeters, but height H may be increased depending on the desired application.

Referring now to FIG. 2, the method of applying magnetic orthodontic retainer system 10 will be described. Mouth 20 is shown including a plurality of teeth 22*a*-22*f*. In one embodiment, a pair of mutually attracted dental modules 14 are placed on opposite sides of delivery member 12, whereby the attractive coupling between mutually attracted dental modules 14 retains them in place on delivery member 12. Mutually attracted dental modules 14 are not bonded to delivery member 12, rather, delivery member 12 functions to carry mutually attracted dental modules 14 to their final destination on adjacent teeth. A quantity of adhesive 16 is then placed on mutually attracted dental modules 14, or, alternatively, adhesive 16 may be applied to mutually attracted dental modules 14 prior to placing modules 14 on opposite sides of delivery member 12. Furthermore, primer material 18 is applied to a posterior surface of adjacent teeth 22, i.e., teeth 22*b* and 22*c*, in a location where adhesive 16 applied to mutually attracted dental modules 14 will contact the surface of teeth 22*b* and 22*c*. Primer material 18 may comprise a material such as acid for etching a posterior surface of each tooth 22. Primer material 18 may also comprise chemical etching or any type of material to facilitate bonding with adhesive 16.

Referring still to FIG. 2, delivery member 12, with mutually attracted dental modules 14 carried thereon, is placed between a pair of adjacent teeth, for example, between teeth 22*b* and 22*c*. Delivery member 12 is then pulled in the general direction of Arrow A, as shown by delivery member 12 being pulled between teeth 22*b* and 22*c*. Arrow A generally indicates an anterior direction, i.e., towards the front of the mouth or from the lingual side of the teeth towards the facial side of the teeth. Delivery member 12 is pulled until the pair of mutually attracted dental modules 14 contacts the teeth, as shown, for example, by mutually attracted dental modules 14 contacting teeth 22*c* and 22*d*. At this point, adhesive 16 contacts primer material 18. Adhesive 16 is then cured to harden adhesive 16 and attach mutually attracted dental modules 14 to teeth 22*c* and 22*d*. In one embodiment, an ultraviolet or visible light source (not shown) may be used to cure adhesive 16.

To complete the operation, delivery member 12 is pulled further anteriorly to remove delivery member 12 from between any teeth, for example, as shown by delivery member 12 removed from between teeth 22*d* and 22*e*. Once delivery member 12 has been completely removed, mutually attracted dental modules 14 remain attached to teeth 22*e* and 22*f*, for example, to provide an orthodontic retainer system. Because mutually attracted dental modules 14 are not secured to delivery member 12 and are only carried thereon via the mutual attraction between mutually attracted dental modules 14, delivery member 12 simply slides between mutually attracted dental modules 14 and the adjacent teeth to which modules 14 are attached for removal of delivery member 12 from mouth 20. Movement of delivery member 12 after curing will not disturb dental modules 14 because the force coupling dental modules 14 to delivery member 12 is less than the force adhering dental modules 14 to the teeth. Once placed, mutually attracted dental modules 14 retain adjacent teeth without the need for other, more cumbersome orthodontic appliances.

Although the above-described embodiments describe mutually attracted dental modules 14, the present disclosure also contemplates a method and apparatus for positioning mutually repelled dental modules 14' (not shown). In this embodiment, mutually repelled dental modules 14' could be positioned on adjacent teeth such that modules 14' repel one another to move the adjacent teeth to a corrected position. Modules 14' could be detachably adhered to delivery member 12 with a force less than the force adhering dental modules 14' to the teeth. In one embodiment, modules 14' may be magnets. If modules 14' comprise magnets, the magnets would be oriented in a repelling, non-attractive position, for example, with the north pole of one module 14' lined up with the north pole of the other module 14'. In contrast and as described above, mutually attracted dental modules 14 would be positioned such that, if modules 14 were magnets, the south pole of one module 14 would line up with the north pole of another module 14, such as to provide an attractive force between the two modules 14. Mutually repelled dental modules 14' could be delivered and positioned on adjacent teeth in the mouth in a substantially identical manner as described above for modules 14.

Figure 4:
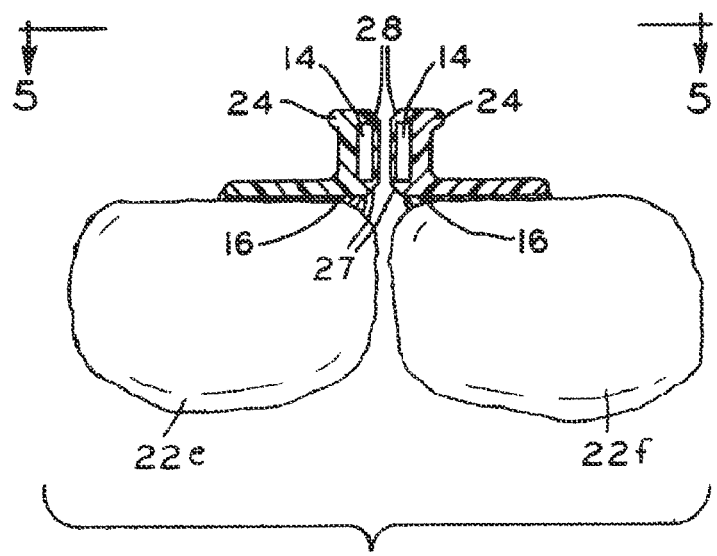
FIG. 4 is an occlusal view of a portion of an individual's teeth, further illustrating the orthodontic retainer system of FIG. 3.
Figure 5:
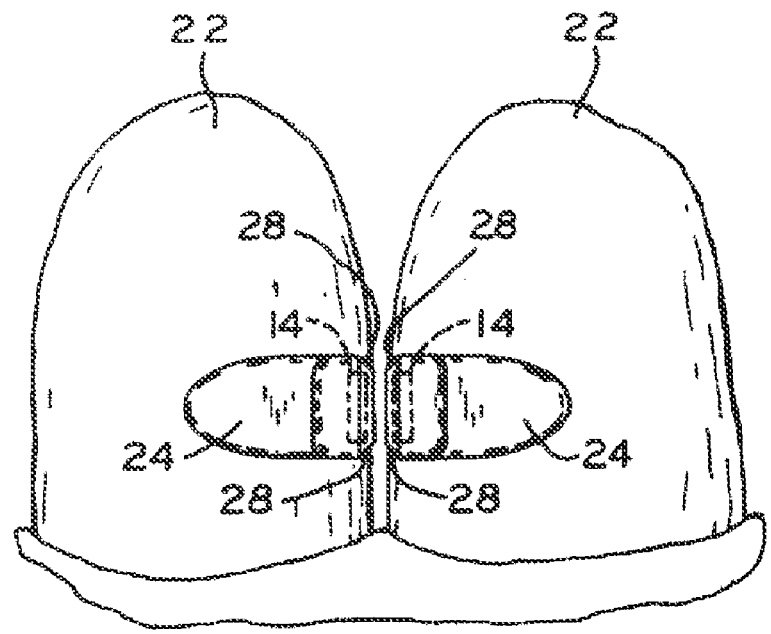
FIG. 5 is a posterior view of the portion of an individual's teeth shown in FIG. 4.
Figure 6:
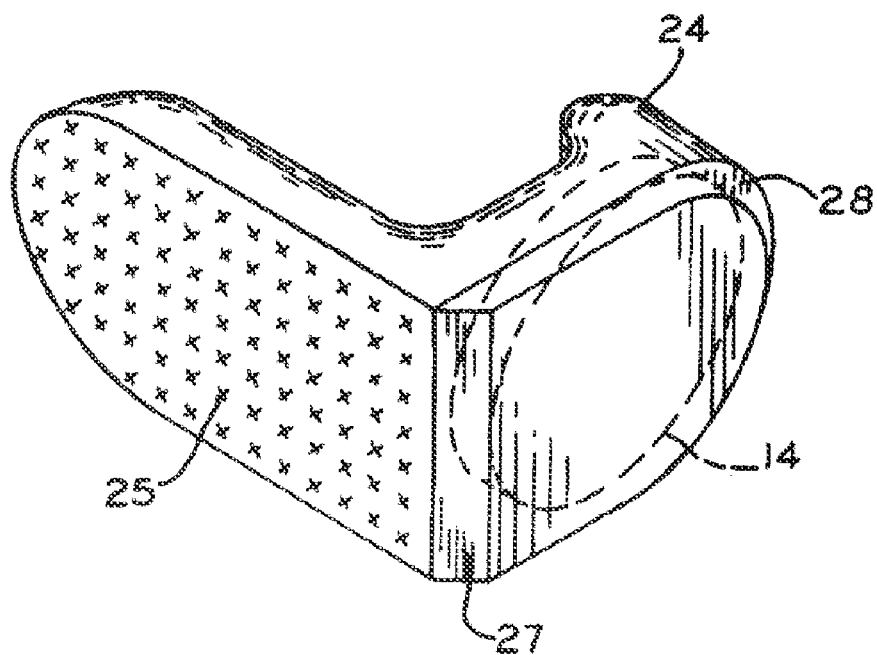
FIG. 6 is a perspective view of a capsule of the present disclosure, further illustrating a mutually attracted dental module encapsulated therein.

Referring now to FIG. 3, in an alternative embodiment, orthodontic retainer system 10' is shown, including strip or delivery member 12 and mutually attracted dental modules 14 encapsulated within capsules 24. Capsules 24 may be formed of metal, ceramic, composite, or any other suitable biocompatible material. In an exemplary embodiment, capsule 24 should not include any sharp edges or irritating features such as features which possibly could cause harm to the tongue or other portions of the mouth. Referring now to FIG. 6, capsule 24 may include surface 25 which facilitates the application of adhesive 16 to capsule 24. Surface 25 may be a grid, mesh, or series of geometric undercuts in capsule 24 to provide an abrasive surface to which adhesive 16 is applied. Capsule 24 may include beveled edge 27 and beveled edge 28. Beveled edges 27 and 28 are provided to facilitate flossing of adjacent teeth 22 after capsules 24 are delivered. Beveled edges 27 and 28 are oriented such that a V-shaped groove is provided on both an upper portion and a lower portion of adjacent capsules 24, as shown in FIG. 5. Beveled edges 27 and 28 are also designed such that a V-shaped groove is provided on both an anterior portion and a posterior portion of adjacent capsules 24, as shown in FIG. 4.

Referring again to FIG. 3, mutually attracted dental modules 14 are used in a substantially identical way as described above wherein mutually attracted dental modules 14 are releasably coupled by attractive forces to opposite sides of delivery member 12.

The method of applying magnetic orthodontic retainer system 10' is substantially identical to the method described above for applying magnetic orthodontic retainer system 10. Referring now to FIGS. 3 and 4, the mutual attraction of mutually attracted dental modules 14 retain both capsule 24 and module 14 in place on delivery member 12. Capsules 24 are not bonded to delivery member 12, rather, capsules 24 are held in place via the mutual attraction of mutually attracted dental modules 14 contained therein. A quantity of adhesive 16 is then placed on capsule 24 on surface 25, or, alternatively, adhesive 16 may be applied to capsule 24 prior to placing capsules 24 and modules 14 on opposite sides of delivery member 12. Furthermore, primer material 18 is applied to a posterior surface of adjacent teeth 22, i.e., teeth 22b and 22c, in a location where adhesive 16 applied to capsules 24 will contact the surface of teeth 22b and 22c. Primer material 18 may comprise a material such as acid for etching a posterior surface of each tooth 22. Primer material 18 may also comprise chemical etching or any type of material to facilitate bonding with adhesive 16.

Similar to the method described above, delivery member 12, with mutually attracted dental modules 14 and capsules 24 carried thereon, is placed between a pair of adjacent teeth, for example, between teeth 22b and 22c. Delivery member 12 is then pulled in the general direction of Arrow A, as shown by delivery member 12 being pulled between teeth 22b and 22c. Delivery member 12 is pulled until the pair of capsules 24 contacts adjacent teeth. At this point, adhesive 16 contacts primer material 18. Adhesive 16 is then cured to harden adhesive 16 and attach capsules 24 to teeth 22. In one embodiment, an ultraviolet or visible light source (not shown) may be used to cure adhesive 16.

To complete the operation, delivery member 12 is pulled further anteriorly to remove delivery member 12 from between any teeth, for example, as shown by delivery member 12 removed from between teeth 22e and 22f. Once delivery member 12 has been completely removed, capsules 24, with mutually attracted dental modules 14 retained therein, remain attached to teeth 22e and 22f, for example, to provide an orthodontic retainer. Because capsules 24 are not secured to delivery member 12 and are only carried thereon via the mutual attraction between mutually attracted dental modules 14, delivery member 12 simply slides between capsules 24 and the adjacent teeth to which capsules 24 are attached for removal of delivery member 12 from mouth 20. Movement of delivery member 12 after curing will not disturb capsules 24 because the force coupling capsules 24 to delivery member 12 is less than the force adhering capsules 24 to the teeth. Once placed, mutually attracted dental modules 14 within capsules 24 retain adjacent teeth without the need for other, more cumbersome orthodontic appliances.

Orthodontic retainer system 10" (not shown) may include capsules 24" made of mutually attractive material. In one embodiment, capsules 24" may be formed as a single entity with no separate mutually attracted dental module contained therein. Capsules 24" could be formed through an injection molding process wherein the entire capsule 24" would be formed into a mutually attracted dental body, for example, a magnet. In one embodiment, capsule 24" may be entirely formed of magnetic material.

Although orthodontic retainer systems 10 and 10' have only been shown as being applied to adjacent anterior teeth in the lower portion of the mouth, the systems may also be applied to any adjacent teeth located anywhere in the mouth. Furthermore, in an alternative embodiment (not shown), orthodontic retainer systems 10 and 10' may be applied in any position on adjacent teeth as opposed to a lingual position as described hereinabove.

The method of application for orthodontic retainer systems 10 and 10' described above may also be used in an alternative, indirect application. In an alternative embodiment, orthodontic retainer system 10 or 10' is applied to an identical, non-human version of mouth 20, for example, a formed mold of mouth 20 including teeth 22. Orthodontic retainer system 10 or 10' is applied to the formed mold of teeth 22 in an identical fashion as described above. After application to the mold, an orthodontist could use any indirect technique commonly known by the dental profession to simultaneously remove all capsules 24 and/or modules 14 and simultaneously apply all capsules 24 and/or modules 14 in the corresponding patient's mouth 20. All capsules 24 and/or modules 14 may be included in a delivery tray or elastic material having the capability to simultaneously move all capsules 24 and/or modules 14 from the mold to mouth 20.

Referring now to FIGS. 7A and 7B, orthodontic retainer system 40 according to another embodiment is shown and may generally include delivery member 42 with handle 43, magnets 44, adhesive 46, and carrier 48. Magnets 44 are releasably coupled by their attractive magnetic forces to opposite sides of delivery member 42. Each magnet 44 may have a first dimension D1 (FIG. 7A), such as a diameter, which may be as small as approximately 0.025, 0.030, 0.035, 0.040, or 0.045 inches or as large as approximately 0.065, 0.060, 0.055, or 0.050 inches, for example. In one form thereof, magnet 44 may be in the shape of a cylinder. Magnet 44 may have a second dimension D2 (FIG. 7B), which may be as small as approximately 0.025, 0.030, 0.035, 0.040, or 0.045 inches or as large as approximately 0.065, 0.060, 0.055, or 0.050 inches, for example. Magnet 44 may also take different shapes or forms, including cross-sectional shapes such as various polygonal shapes. Each magnet 44 may be formed of a biocompatible material to allow its implantation in the mouth for a period of time. For example, each magnet 44 may be formed either partially or completely of gold or neodymium iron.

Delivery member 42 may be substantially similar to delivery members 12, 112 described above, except as described below. For example, delivery member 42 may be a thin, non-magnetic strip of material, such as Mylar® material, having a thickness T which, in one embodiment, may be as small as 0.001, 0.002, 0.003, 0.004, or 0.005 inches or as large as approximately 0.012, 0.011, 0.010, 0.009, 0.008, 0.007, or 0.006 inches, for example. Thickness T is such as to allow delivery member 42 to pass between a pair of adjacent teeth 50a, 50b. Delivery member 42 may also be formed of a flexible plastic material, such as Mylar® material, for example, or, alternatively, a metal material, such as stainless steel, for example. In one embodiment, delivery member 42 includes a release coating, for example, a silicone, polyethylene, or fluoropolymer coating, such as polytetrafluoroethylene (PTFE) which is commercially available as Teflon® from E. I. du Pont de Nemours and Company of Wilmington, Del.; Silicon Premium, a siloxane release coating commercially available from General Electric Company of Waterford, N.Y.; and Clearsil® fluorosilicone release films and ClearLES™ silicone release liners commercially available from CPFilms, Inc. of Martinsville, Va. The length of delivery member 42 can be any size to facilitate an easy access for an orthodontist for pulling delivery member 42 between a pair of adjacent teeth 50a, 50b. Delivery member 42 may include handle 43 to facilitate movement of delivery member 42.

Adhesive 46 may be substantially similar to adhesive 16, described above with reference to FIGS. 1-4, except as described below. Magnets 44 may be at least partially encapsulated within, or enveloped by, adhesive 46. Adhesive 46 may be any adhesive suitable for a dental application, such as OptiBond®, available from Kerr Corporation of Orange, Calif.; Adper™ and Scotchbond™ adhesives available from 3M Corporation of St. Paul, Minn.; or Xeno® Light Cured Dental Adhesive available from DENTSPLY of York, Pa.

Carrier 48 may include recess 49 defining inner surface 51. Inner surface 51 conforms around magnet 44 and adhesive 46 and, after carrier 48 is removed in the manner described below, defines surface 47 of adhesive 46, which is an envelope or profile of adhesive surrounding magnets 44. Adhesive 46 at least partially surrounds magnets 44 within recess 49. Inner surface 51 may be formed with a generally smooth surface with no protrusions or other edges such that the profile of adhesive 46 thereby created also includes only a smooth surface with no protruding edges for patient comfort after removal of carrier 48 therefrom. In an exemplary embodiment, carrier 48 is formed of a water soluble material, such as polyvinyl alcohol (PVOH) or other water soluble polymer, for example. Carrier 48 may be formed of a material which does not bond with adhesive 46 and which may be removed from adhesive 46 after curing of adhesive 46.

In operation and referring to FIG. 8, the method of using magnetic orthodontic retainer system 40 will be described. To begin, recess 49 of carrier 48 is at least partially filled with adhesive 46. Adhesive 46 may be in the form of a viscous liquid at this stage and magnets 44 are at least partially embedded therein. Adhesive 46 fills recess 49 such that surface 47 of adhesive 46 substantially matches inner surface 51 of recess 49. At this point, adhesive 46 may optionally be partially cured, or pre-cured, with a suitable curing instrument, such as those described below, such that adhesive 46 is a highly viscous or substantially solid material, i.e., in a non-liquid state, to facilitate delivery to teeth 50a, 50b. Magnets 44, along with adhesive 46 and carrier 48, are releasably coupled by attractive forces to opposite sides of delivery member 42, as shown in FIG. 7A. Magnets 44, adhesive 46, and carrier 48 are not bonded to delivery member 42, rather, delivery member 42 functions to carry magnets 44 to their final destination on adjacent teeth. A release coating on delivery member 42, as described above, may further reduce the possibility of adhesive 46 or carrier 48 bonding to delivery member 42. A quantity of primer material (not shown), similar to primer material 18, described above with reference to FIG. 3, may be applied to a lingual surface of adjacent teeth 50a, 50b in a location where adhesive 46 will contact the lingual surface of teeth 50a, 50b.

Figure 9:
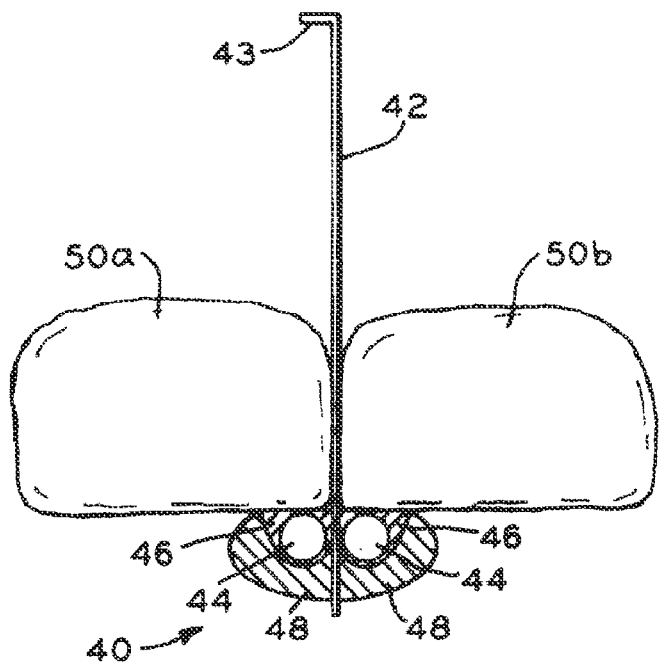

Delivery member 42, with magnets 44 carried thereon, is placed between a pair of adjacent teeth, for example, between teeth 50a, 50b. Delivery member 42 is then pulled via handle 43, for example, in the general direction of Arrow B (FIG. 8), as shown by delivery member 42 being pulled between teeth 50a, 50b. Arrow B generally indicates a direction away from the lingual side of the teeth and toward the facial side of the teeth. Delivery member 42 is pulled until adhesive 46 and/or magnets 44 contact the lingual surfaces of teeth 50a, 50b, as shown in FIG. 9.

Figure 10:
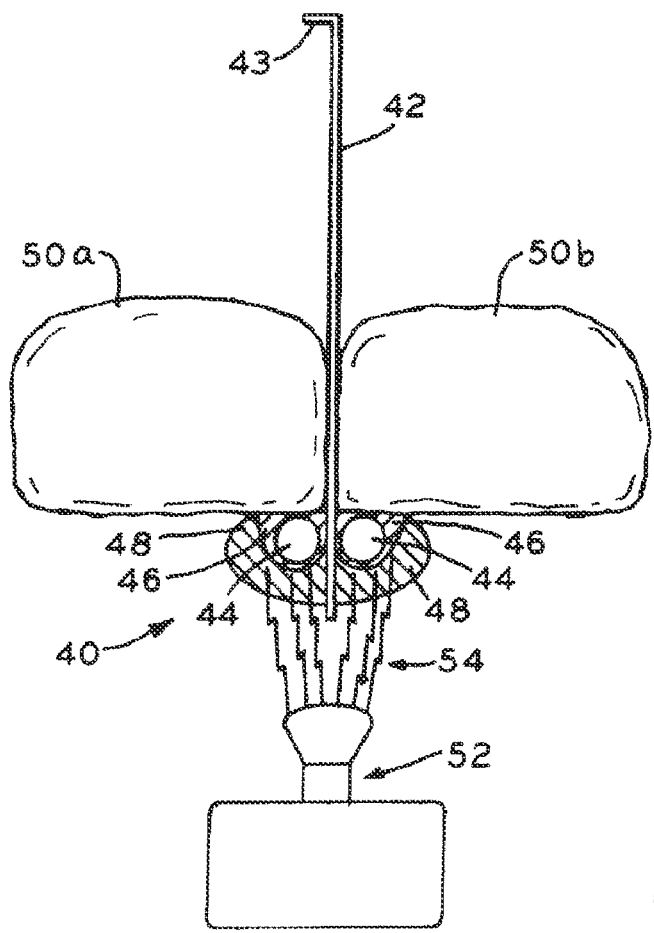

As shown in FIG. 10, adhesive 46 is then fully cured to completely harden adhesive 46 and thereby attach magnets 44 to teeth 50a, 50b. In one embodiment, curing instrument 52 may be used to cure adhesive 46 using curing rays 54. In an exemplary embodiment, curing rays 54 are light rays and curing instrument 52 is a light-based curing instrument. In one embodiment, the light rays are ultraviolet (UV) rays and the light-based curing instrument is a UV-based curing instrument. Examples of light-based curing instruments include the SmartLite®PS LED Curing Light and the Spectrum® 800 Curing Unit with Intensity Control, both available from DENTSPLY of York, Pa. Curing of adhesive 46 solidifies adhesive 46 and securely attaches adhesive 46 and magnets 44 to each of teeth 50a, 50b. Curing of adhesive 46 within recess 49 of carrier 48 ensures that adhesive 46 has a profile substantially matching inner surface 51 of recess 49. The profile of adhesive 46 advantageously has no edges or protrusions and provides a smooth and non-irritating lingual surface 47, as described further below.

Figure 11:
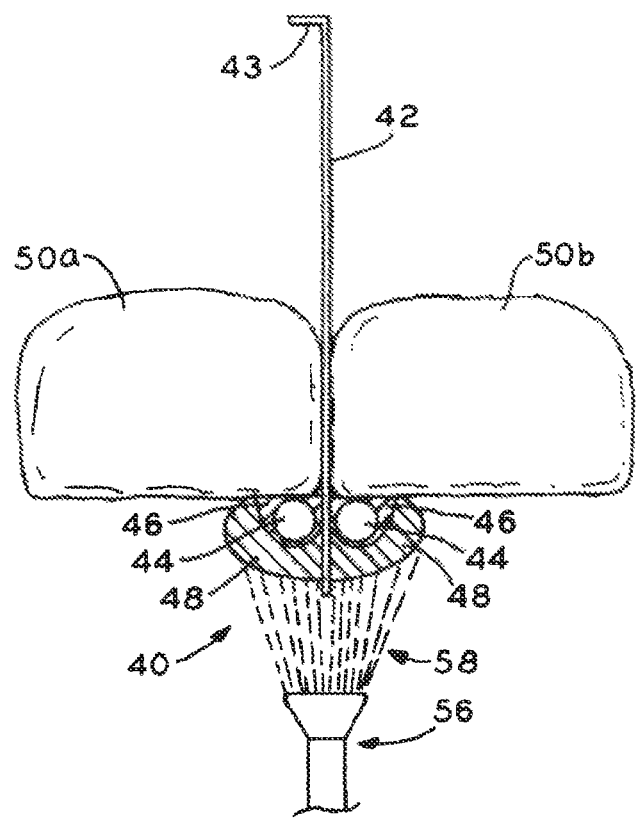
Figure 12:
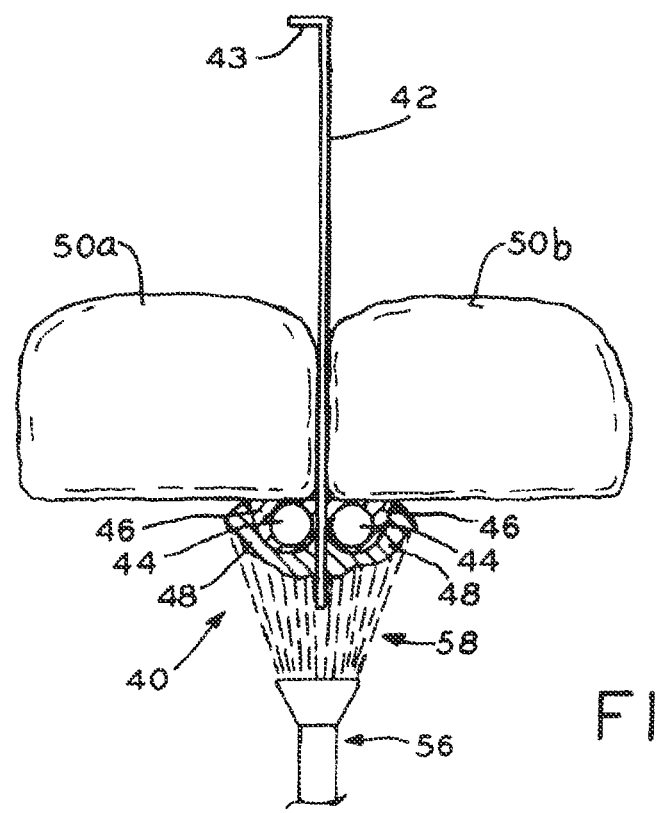

Referring to FIG. 11, carrier 48 may be removed from adhesive 46 to reveal surface 47 which has a substantially smooth profile. Carrier 48 shown in FIG. 11 may be formed of a water soluble material, such as a water soluble polymer, i.e., polyvinyl alcohol (PVA or PVOH), for example. Water source 56 may supply an amount of water 58 or other water-based solution onto carrier 48. Water source 56 may be any suitable water supply instrument, such as the Waterpik® Dental Water Jet, available from Waterpik Technologies, Inc. of Newport Beach, Calif.; and the Interplak® Dental Water jet, available from Conair of Stamford, Conn., for example. Because carrier 48 is formed of a water-soluble material, application of water 58 dissolves carrier 48. As shown in FIG. 12, carrier 48 is partially dissolved. In one embodiment, suction may be applied adjacent water source 56 to remove water 58 and portions of carrier 48 which are dissolved. Carrier 48 may be formed of a material that is not harmful if swallowed.

Figure 13:
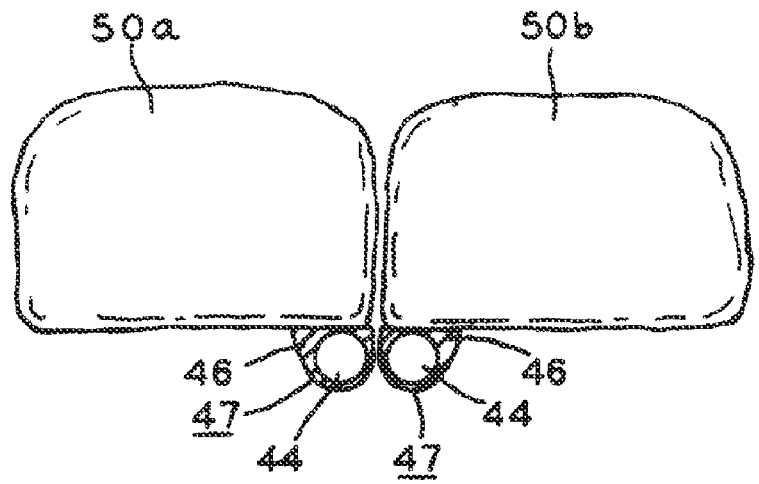

Referring to FIG. 13, further application of water 58 substantially and completely dissolves carrier 48 (FIGS. 11 and 12) such that adhesive 46 and magnets 44 are the only portion of system 40 to remain. Dissolving carrier 48 reveals a smooth lingual surface 47 of adhesive 46 defining a smooth profile of adhesive 46 which is completely cured to secure magnets 44 to teeth 50a, 50b. In an exemplary embodiment, lingual surface 47 of adhesive 46 is a substantially smooth surface with no sharp edges or projections. Such a smooth surface facilitates comfort for the patient. Advantageously, adhesive 46 requires no post-curing formation, such as by removing and/or manually forming adhesive 46 around magnets 44 to obtain a desired profile of adhesive 46, thereby greatly reducing the time needed for an orthodontist to apply magnets to a patient's dentition. For example, if the orthodontist has a large number of magnets to apply, system 40 greatly reduces the time required for such a procedure. The present method eliminates such post-curing formation and provides a fully cured and shaped profile for adhesive 46 which is both comfortable for a user of system 40 and is aesthetically pleasing. The shaped profile of adhesive 46 advantageously provides a comfortable retainer system for the patient and blends into the surrounding teeth proximate teeth 50a, 50b. Furthermore, adhesive 46 may be colored such that, when fully cured, adhesive 46 is substantially the same color as teeth 50a, 50b to which adhesive 46 is secured.

To complete the operation, delivery member 42 may be pulled and/or otherwise removed from between teeth 50a, 50b. Once delivery member 42 has been completely removed, magnets 44 with adhesive 46 remain attached to teeth 50a, 50b, for example, to provide an orthodontic retainer system, as shown in FIG. 13. Because magnets 44 and adhesive 46 are not secured to delivery member 42 and are only carried thereon via the mutual attraction between magnets 44, delivery member 42 simply slides between magnets 44 and adhesive 46 and the adjacent teeth to which adhesive 46 and magnets 44 are attached for removal of delivery member 42 from the mouth of the patient. Movement of delivery member 42 after curing of adhesive 46 will not disturb adhesive 46 and magnets 44 because the force coupling magnets 44 and adhesive 46 to delivery member 42 is less than the force adhering adhesive 46 and magnets 44 to the teeth. Once fixed in position, magnets 44 retain adjacent teeth without the need for other, more cumbersome orthodontic appliances. Although described above as removing delivery member 42 after removal of carrier 48, practice of the present method may alternatively involve removal of delivery member 42 first, followed by removal of carrier 48.

Figure 14:
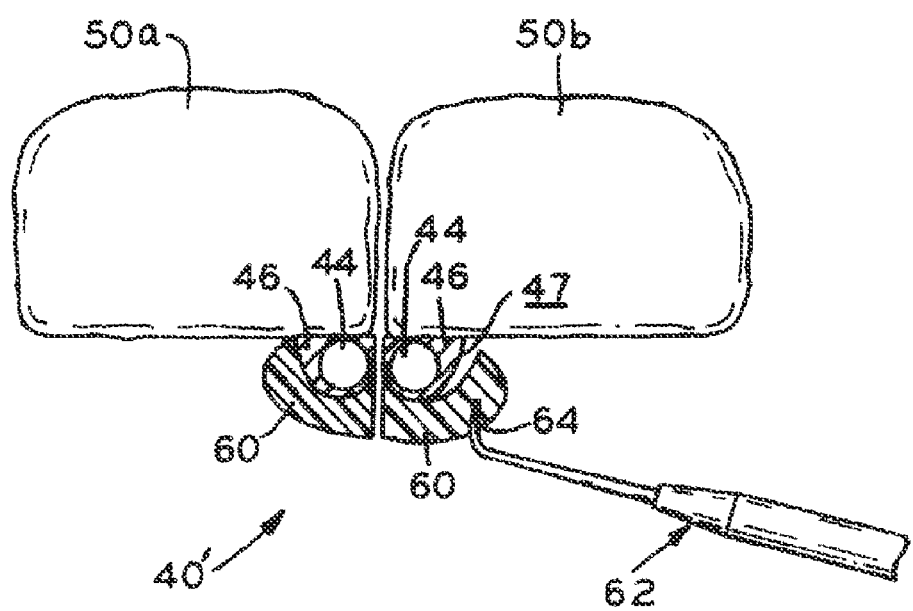
Figure 22:
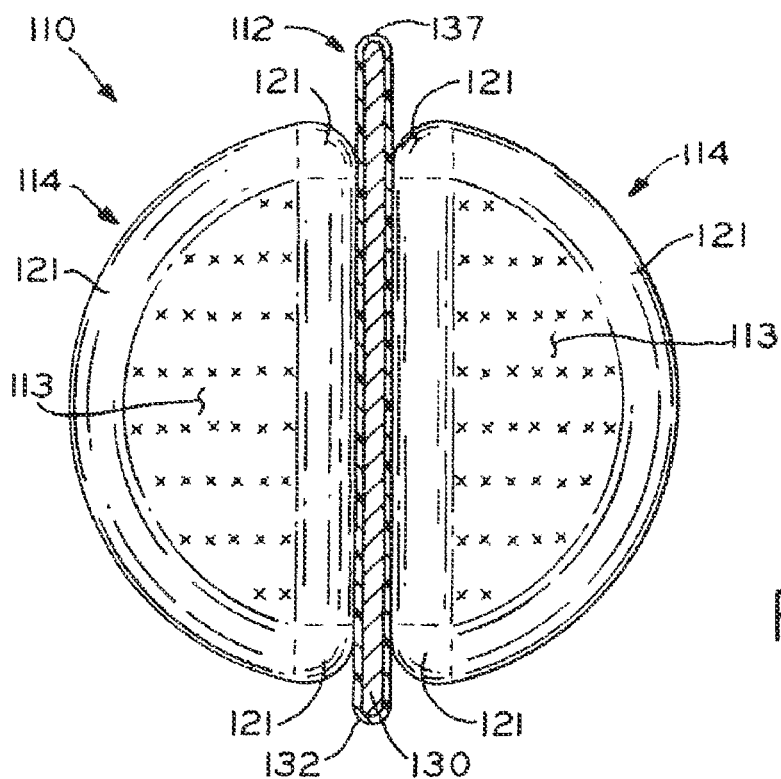
FIG. 22 is a cross-sectional view of the delivery member of FIG. 21 taken along line 22-22 of FIG. 21, further illustrating the pair of coupled mutually attractive members of FIG. 21.
Figure 23:
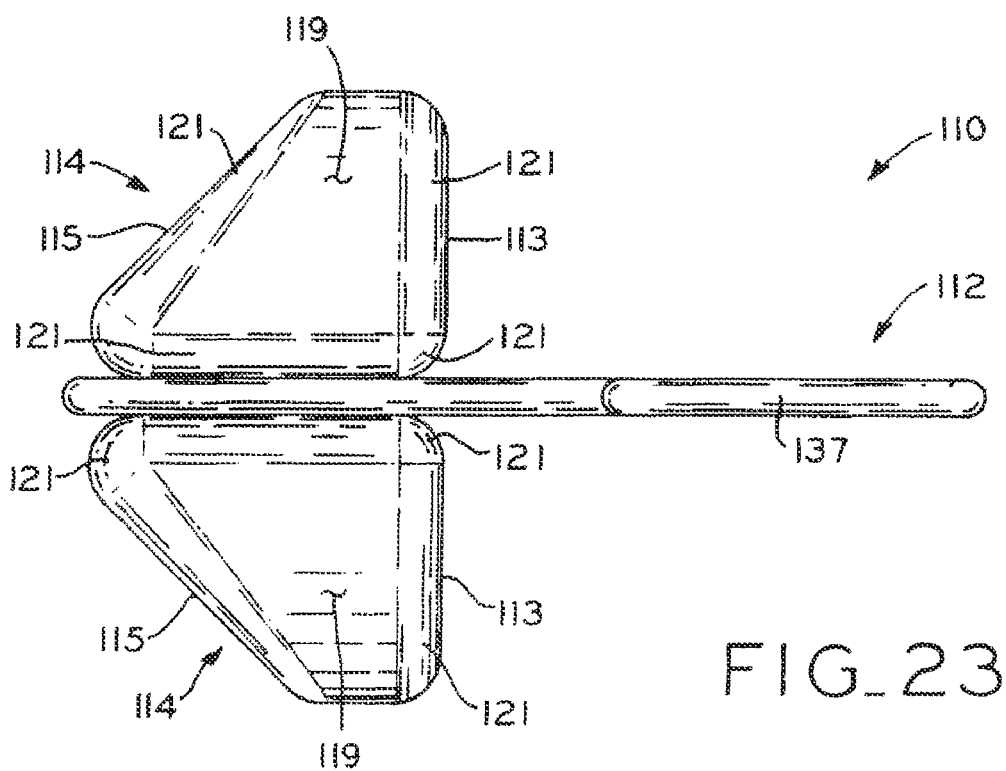
FIG. 23 is an occlusal view of the delivery member and pair of coupled mutually attractive members of FIG. 21 from the perspective of line 23-23 of FIG. 21.

Referring to FIG. 14, an alternative embodiment retainer system 40' is shown and generally includes delivery member 42 with handle 43, magnets 44, adhesive 46, and carrier 60. Carrier 60 may be formed of a flexible material which does not bond with adhesive 46 and which may be removed from adhesive 46 after curing of adhesive 46. In an exemplary embodiment, carrier 60 is formed of a flexible silicone-based material which may be peeled off adhesive 46 using scaler 64 or another suitable dental instrument 62. Scaler 64 may pierce carrier 60 after which carrier 60 is peeled or pulled away from adhesive 46 to reveal the substantially smooth envelope or profile of adhesive 46, as described above. Alternatively, carrier 60 may be removed via any other instrument or by hand. For example, dental instrument 62 may include forceps which are used to grasp a portion of carrier 60 and remove carrier 60 to reveal the profile of adhesive 46.

Referring now to FIG. 21, orthodontic retainer system 110 is shown, including strip or delivery member 112 and mutually attracted dental modules 114. While described and depicted herein with specific references to dental modules 114, delivery member 112 may also be used in conjunction with other dental modules described herein, such as dental modules 14 described above. Similarly, while described and depicted herein with specific references to delivery member 112, dental modules 114 may also be used in conjunction with other delivery members described herein, such as delivery member 12 described above. Mutually attracted dental modules 114 are releasably coupled by attractive forces to opposite sides of delivery member 112. For example, in one embodiment, each mutually attracted dental module 114 may comprise a magnet or any other suitable device capable of mutual attraction, i.e., electrostatic members. When mutually attracted dental modules 114 are magnets, they are coupled together on delivery member 112 via magnetic forces. Each mutually attracted dental module 114 has a dimension D3 (FIG. 18), such as a height, which may be as small as 0.010, 0.015, 0.020, or 0.025 inches or as large as 0.030, 0.035, 0.040, or 0.045 inches, for example. In one exemplary embodiment, dimension D3 is 0.040 inches.

Referring to FIGS. 15-18, in one exemplary embodiment, mutually attracted dental module 114 has a substantially polygonal or trapezoidal shape in cross-section taken along a direction perpendicular to tooth engaging surface 113, as best shown in FIG. 17. Specifically, tooth engaging surface 113, lingual surface 115, and bottom surface 117 are substantially planar surfaces. Curved top surface 119, in conjunction with rounded and/or chamfered corners 121, joins each of tooth engaging surface 113, lingual surface 115, and bottom surface 117 to one another. Additionally, dental module 114 has a width W (FIG. 18) that corresponds to the distance between opposing ends of bottom surface 117. Similarly, the radius of curvature of top surface 119 corresponds to the width of dental module 114 and extends between the opposing ends of bottom surface 117. In one exemplary embodiment, the radius of curvature of top surface 119 is 0.040 inches. However, the radius of curvature of top surface 119 may be as small as 0.020, 0.025, 0.030, or 0.035 inches or as large as 0.040, 0.045, 0.050, or 0.055 inches, for example. In one exemplary embodiment, lingual surface 115 forms an angle α with the apex of top surface 119. In one exemplary embodiment, angle α is approximately 45 degrees. However, angle α may be as small as 20, 25, 30, 35, or 40 degrees or as large as 45, 50, 55, 60, and 65 degrees, for example. Advantageously, by angling lingual surface 115 and utilizing rounded corners 121, the comfort of the patient is facilitated, and the patient may floss between adjacent teeth on which dental modules 114 are attached without cutting the floss.

In another exemplary embodiment, tooth engaging surface 113 is modified to facilitate the retention of an adhesive thereon. For example, tooth engaging surface 113 may include a grid, mesh, or series of geometric undercuts to provide an abrasive surface to which adhesive 16, 46 (FIG. 24) is applied. In another exemplary embodiment, tooth engaging surface 113 may include a coating formed by chemical vapor deposition (CVD). Each mutually attracted dental module 114 is made of a biocompatible material to allow its implantation in the mouth for a period of time. For example, referring to FIGS. 17 and 18, in one exemplary embodiment, each mutually attracted dental module 114 has an outer coating 123, such as gold-plating, substantially entirely surrounding inner magnet 129. In one exemplary embodiment, inner magnet 129 is comprised of a permanent magnet, such as a rare-earth magnet. In one exemplary embodiment, inner magnet 129 is a neodymium-iron-boron magnet. In another exemplary embodiment, module 114 lacks outer coating 123.

Referring to FIGS. 19-21, delivery member 112 may be substantially similar to delivery member 12, described above with reference to FIGS. 1-3, except as described below. For example, delivery member 112 may also be formed of a flexible plastic material, such as Mylar® material, for example, or, alternatively, a metal material, such as stainless steel, for example. In one embodiment, delivery member 112 includes core 130, formed from a material described above, and release coating 132 substantially surrounding core 130. For example, release coating 132 may be a silicone, polyethylene, or fluoropolymer coating, such as polytetrafluoroethylene (PTFE) which is commercially available as Teflon® from E. I. du Pont de Nemours and Company of Wilmington, Del.; Silicon Premium, a siloxane release coating commercially available from General Electric Company of Waterford, N.Y.; and Clearsil® fluorosilicone release films and ClearLES™ silicone release liners commercially available from CPFilms, Inc. of Martinsville, Va.

Additionally, as shown in FIGS. 19-21, delivery member 112 has a substantially L-shape including gripping portion 131 and retention portion 133. Longitudinal gripping portion axis GPA intersects longitudinal retention portion axis RPA to form the substantially L-shape, wherein the intersection of longitudinal gripping portion axis GPA and longitudinal retention portion axis RPA results in the formation of angle β. In one exemplary embodiment, angle β is equal to 90 degrees or is any acute angle greater than 30 degrees and less than 90 degrees. As shown in FIG. 19, in one exemplary embodiment, angle β is 80 degrees. Additionally, to facilitate patient comfort during the delivery of dental modules 114, gripping portion 131 and retention portion 133 have rounded and/or chamfered corners 135. In one exemplary embodiment, shown in FIG. 20, periphery 137 of delivery member 112 also has a bulbous or rounded shape to further facilitate patient comfort during the delivery of dental modules 114. Gripping portion 131 may also include a grid, mesh, or series of geometric undercuts 139, shown in FIG. 19, to provide an abrasive surface upon which a orthodontist may grasp either directly by hand or indirectly through the use of dental instruments.

Delivery member 112 has a height H2 that may be a small as 0.25, 0.30, 0.35 or 0.40 inches or as large as 0.45, 0.50, 0.75, or 1.00 inches, for example. The length of delivery member 112 can be any size to facilitate easy access for an orthodontist for pulling delivery member 112 between a pair of adjacent teeth 20a and 20b, as described in detail below. In exemplary embodiments, delivery member 112 may have a length L as small as 0.25, 0.30, 0.35 or 0.40 inches or as large as 0.45, 0.50, 0.75, or 1.00 inches, for example. Additionally, retention portion 133 of delivery member 112 has a height H3. In exemplary embodiments, height H3 of retention member 133 is as small as 0.10, 0.15, 0.20 or 0.25 inches or as large as 0.30, 0.35, 0.40, or 0.45 inches, for example. In an alternative embodiment, delivery member 112 may be part of a continuous piece of material which has pairs of mutually attracted dental modules 114 carried thereon at various spaced distances and may operate in the same manner as described in detail above with reference to delivery member 12. Further, delivery member 112 may also include scribe marks 116, shown in FIGS. 19 and 21, which may be lettered or numbered accordingly to provide a depth gauge, thereby providing the orthodontist with an indication of the depth of delivery member 112 with respect to adjacent teeth 22.

Except as described below, the method of applying magnetic orthodontic retainer system 110 is similar to the method described above for applying magnetic orthodontic retainer systems 10, 10". Referring now to FIGS. 22-27, the mutual attraction of mutually attracted dental modules 114 retains both modules 114 in place on delivery member 112. A quantity of adhesive 16, 46, described in detail above, is then placed on tooth engaging surface 113 of dental modules 114. In another exemplary embodiment, adhesive 16, 46 may be placed on dental modules 114 prior to retaining dental modules 114 on delivery member 112. Alternatively, adhesive 16, 46 may be applied directly to adjacent teeth, such as teeth 22, i.e., teeth 22a and 22b. Furthermore, in one exemplary embodiment, primer material 18 (FIG. 3) is applied to a posterior surface of adjacent teeth 22, i.e., teeth 22a and 22b, in a location where adhesive 16, 46 applied to dental modules 114 will contact the surface of teeth 22a and 22b. Primer material 18 may comprise a material such as acid for etching a posterior surface of each tooth 22. Primer material 18 may also comprise chemical etching or any type of material to facilitate bonding with adhesive 16, 46.

Figure 28A:
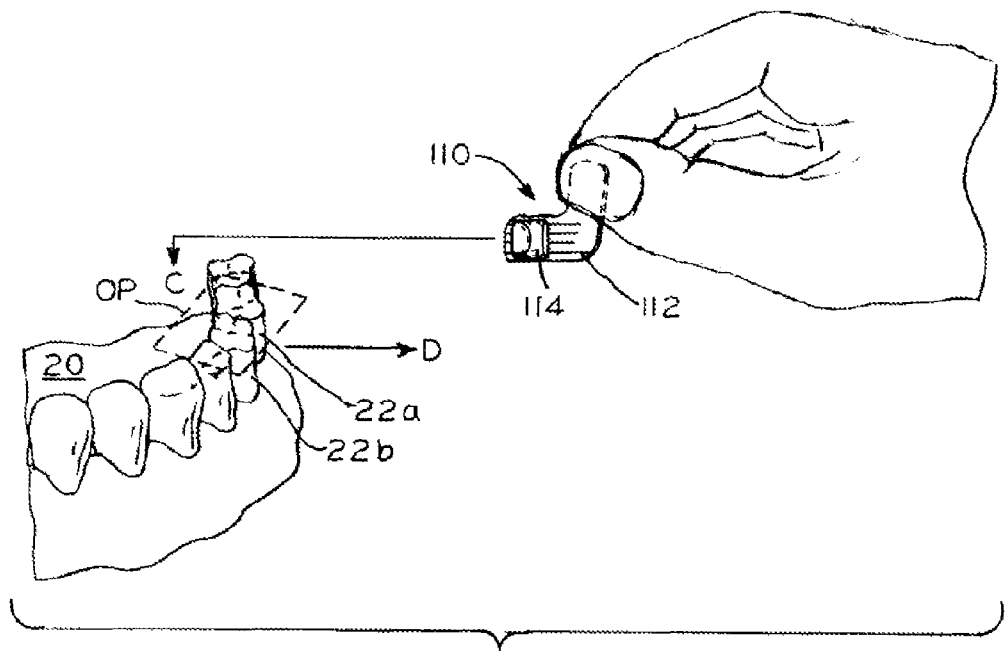
FIG. 28A is a perspective view of a portion of a patient's mouth, further depicting a partial perspective view of an orthodontist's hand grasping the delivery member of FIG. 19 having a mutually attractive member according to FIG. 15 positioned thereon.
Figure 28B:
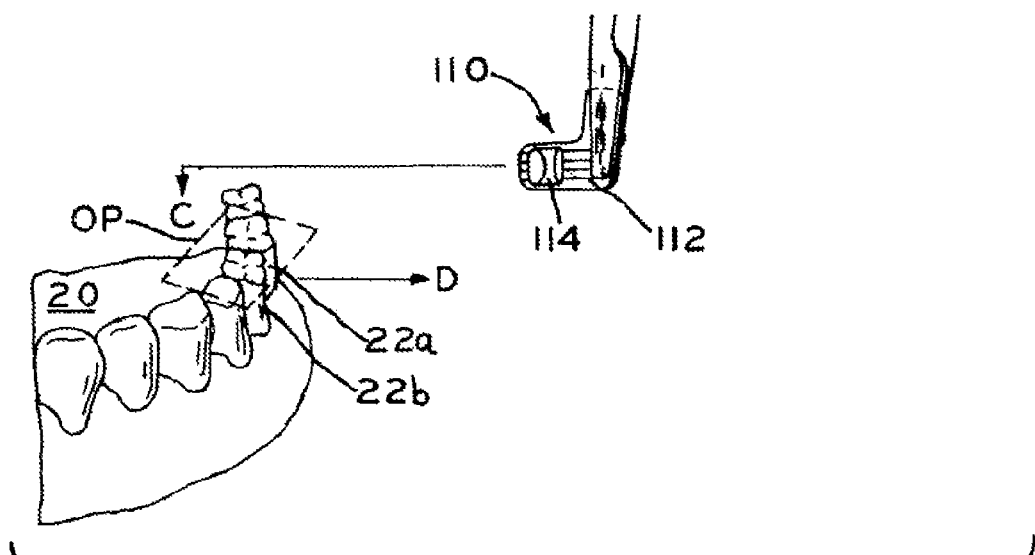
FIG. 28B is a perspective view of a portion of a patient's mouth, further depicting a partial perspective view of an orthodontic instrument grasping the delivery member of FIG. 19 having a mutually attractive member according to FIG. 15 positioned thereon.

Similar to the method described above, delivery member 112, with mutually attracted dental modules 114 carried thereon, is placed between a pair of adjacent teeth, for example, between teeth 22a and 22b. Referring to FIG. 28, in one exemplary embodiment, the orthodontist grasps gripping portion 131, either directly by hand or indirectly with an orthodontic instrument, and positions retention portion 133 between teeth 22a and 22b, while the orthodontist's fingers and/or instrument remain substantially outside the oral cavity and outwardly of occlusal plane OP defined by the occlusal surfaces of teeth 22a and 22b. Specifically, referring to FIG. 28, the orthodontist moves delivery member 112 inwardly into the patient's oral cavity and then downwardly between teeth 22a and 22b, as shown by Arrow C. Delivery member 112 is then pulled in the general direction of Arrow D, resulting in delivery member 112 being pulled between teeth 22a and 22b. During movement of delivery member 112, the orthodontist's fingers and/or instrument remain substantially outside the patient's oral cavity and outwardly of occlusal plane OP of teeth 22a and 22b. Delivery member 112 is pulled until tooth engaging surfaces 113 of dental modules 114 contact adjacent teeth. At this point, adhesive 16, 46 contacts primer material 18. Adhesive 16, 48 may then be cured to harden adhesive 16, 46 and attach dental modules 114 to teeth 22. In one embodiment, an ultraviolet or visible light source, such as those described in detail above with reference to adhesive 46, may be used to cure adhesive 16, 46.

To complete the operation, delivery member 112 is pulled further anteriorly to remove delivery member 112 from between teeth 22a and 22b. Due to the substantially L-shape of delivery member 112, the need for the orthodontist to manipulate or otherwise move and/or grasp the patient's lip, tongue, and/or cheek to facilitate removal of delivery member 112 is substantially eliminated. Once delivery member 112 has been completely removed, mutually attracted dental modules 114 remain attached to teeth 22a and 22b to provide an orthodontic retainer. Because modules 114 are not secured to delivery member 112 and are only carried thereon via the mutual attraction between mutually attracted dental modules 114, delivery member 112 simply slides between the adjacent teeth for removal of delivery member 112 from mouth 20 (FIG. 2). Movement of delivery member 112 after curing will not disturb dental modules 114 because the force coupling dental modules 114 to delivery member 112 is less than the force adhering dental modules 114 and adhesive 16, 46 to the teeth. Once placed, mutually attracted dental modules 114 retain adjacent teeth without the need for other, more cumbersome orthodontic appliances. In another exemplary embodiment, orthodontic retainer system 110' (not shown) may include capsules 24, 24", as described in detail herein.

Although orthodontic retainer systems 110, 110' have been shown and illustrated herein as being applied to adjacent teeth in the lower portion of the mouth, i.e., to teeth in the mandibular arch, the systems may of course be applied to adjacent teeth in the upper portion of the mouth, i.e., to teeth in the maxillar arch, by simply inverting delivery member 112 and dental modules 114. Furthermore, in an alternative embodiment (not shown), orthodontic retainer systems 110, 110' may be applied in any position on adjacent teeth as opposed to the lingual position as described and illustrated herein.

The method of application for orthodontic retainer systems 110, 110' described above may also be used in an alternative, indirect application. In an alternative embodiment, orthodontic retainer system 110, 110' is applied to an identical, non-human version of mouth 20, for example, a formed mold of mouth 20 including teeth 22. Orthodontic retainer system 110, 110' is applied to the formed mold of teeth 22 in an identical fashion as described above. After application to the mold, an orthodontist could use any indirect technique commonly known by the dental profession to simultaneously remove all capsules 24, 24" and/or modules 14, 114 and simultaneously apply all capsules 24 and/or modules 14, 114 in the corresponding patient's mouth 20. All capsules 24, 24" and/or modules 14, 114 may be included in a delivery tray or elastic material having the capability to simultaneously move all capsules 24, 24" and/or modules 14, 114 from the mold to mouth 20.

While this disclosure has been described as having exemplary designs, the present disclosure may be further modified within the spirit and scope of this disclosure. This application is therefore intended to cover any variations, uses, or adaptations of the disclosure using its general principles.

What is claimed is:

1. An orthodontic retainer system for use on teeth, comprising:
    a delivery member, comprising:
        a gripping portion having a height extending along a gripping portion axis, said height between 0.25 inches and 1.00 inches; and
        a retention portion having a length extending along a retention portion axis, said length between 0.25 inches and 1.00 inches, a ratio of said height to said length between about 0.25 and 4, said gripping portion joined to said retention portion at an angle such that said delivery member is substantially L-shaped; and
    a pair of magnetic, mutually attractive dental modules coupled to said delivery member solely by mutual magnetic attraction of said magnetic dental modules, said magnetic dental modules including planar surfaces in direct contact with respective opposite sides of said retention portion of said delivery member, said delivery member adapted to deliver said dental modules between a pair of adjacent teeth.

2. The retainer system of claim 1, wherein said gripping portion axis and said retention portion axis are substantially perpendicular.

3. The retainer system of claim 1, wherein said gripping portion axis and said retention portion axis define an acute angle greater than thirty degrees and less than ninety degrees.

4. The retainer system of claim 1, wherein said delivery member comprises a substantially thin piece of flexible material having a thickness between 0.001 and 0.006 inches.

5. The retainer system of claim 1, wherein said retention portion of said delivery member further comprises a height of between 0.10 inches and 0.45 inches.

6. The retainer system of claim 1, wherein at least said retention portion of said delivery member includes a core, said core covered by a release coating.

7. The retainer system of claim 1, wherein each of said magnetic dental modules comprises a rare earth magnet and a coating surrounding said rare earth magnet.

8. The retainer system of claim 7, wherein said rare earth magnet is a neodymium-iron-boron magnet and said coating is a gold coating.

9. The orthodontic retainer system of claim 1, wherein said magnetic dental modules each define a dental module height, and said delivery member further comprises a delivery member height defined along said gripping portion axis, said dental module height being less than said delivery member height.

10. The retainer system of claim 1, wherein said delivery member is formed from one of a plastic material and a metal material.

11. The retainer system of claim 10, wherein said delivery member is formed from stainless steel.

12. An orthodontic retainer system for use on teeth, comprising:
    a substantially L-shaped delivery member formed from stainless steel, comprising:
        a gripping portion having a height extending along a gripping portion axis, said height between 0.25 inches and 1.00 inches; and
        a retention portion having a length extending along a retention portion axis, said length between 0.25 inches and 1.00 inches, said gripping portion and said retention portion co-planar and extending substantially perpendicular to one another,
        said L-shaped delivery member having a thickness extending perpendicularly to said retention portion axis and said gripping portion axis, said thickness between 0.001 and 0.012 inches; and
    a pair of magnetic, mutually attractive dental modules coupled to said delivery member solely by mutual magnetic attraction of said magnetic dental modules, said magnetic dental modules including planar surfaces in direct contact with respective opposite sides of said retention portion of said delivery member, said delivery member adapted to deliver said dental modules between a pair of adjacent teeth.

13. The retainer system of claim 12, wherein said retention portion of said delivery member further comprises a delivery member height of between 0.10 inches and 0.45 inches.

14. The orthodontic retainer system of claim 13, wherein said magnetic dental modules each define a dental module height, said dental module height being less than said delivery member height.

15. The orthodontic retainer system of claim 12, wherein said height and said length are each about 0.38 inches.

16. A method of applying a pair of magnetic, mutually attractive dental modules to a pair of adjacent teeth each having a lingual side, comprising the steps of:
    providing a substantially L-shaped delivery member having a retention portion and a gripping portion that are co-planar and extend substantially perpendicular to one another;
    coupling the magnetic dental modules to respective opposite sides of the retention portion of the delivery member with the magnetic dental modules retained against the opposite sides solely by mutual magnetic attraction of the magnetic dental modules;
    gripping the gripping portion of the delivery member and orienting the delivery member with the retention portion extending in a direction substantially parallel to an occlusal plane defined by the pair of adjacent teeth, and the gripping portion extending in a direction substantially perpendicular to the occlusal plane;
    inserting the retention portion of the delivery member between the pair of adjacent teeth with the gripping portion remaining on a side of the occlusal plane opposite the pair of adjacent teeth and extending outwardly of the occlusal plane;
    securing, respectively, the pair of magnetic dental modules to the pair of adjacent teeth; and
    removing the retention portion of the delivery member from between the pair of adjacent teeth.

17. The method of claim 16, further comprising the additional step, after said inserting step and prior to said securing step, of advancing the delivery member in an anterior direction until the magnetic dental modules contact respective lingual sides of the pair of adjacent teeth.

18. The method of claim 17, further comprising the step of positioning adhesive material on tooth engaging surfaces of the magnetic dental modules, wherein said first advancing step further comprises abutting the adhesive material with the lingual sides of the teeth.

19. The method of claim 18, further comprising the step during said step of gripping the gripping portion of the delivery member, of curing the adhesive material.

20. The method of claim 18, wherein said gripping step comprises manually gripping the gripping portion of the delivery member.

21. The method of claim 18, wherein said gripping step comprises gripping the gripping portion of the delivery member with a dental instrument.

* * * * *